US00PP11688P

United States Patent [19]

van Andel

[11] Patent Number: Plant 11,688

[45] Date of Patent: Dec. 12, 2000

[54] ALSTROEMERIA PLANT NAMED 'STALSIMO'

[75] Inventor: Jacob van Andel, Aalsmeer, Netherlands

[73] Assignee: Van Staaveren B.V., Aalsmeer, Netherlands

[21] Appl. No.: 09/226,020

[22] Filed: Jan. 6, 1999

[51] Int. Cl.[7] ..... A01H 5/00

[52] U.S. Cl. ..... Plt./309

[58] Field of Search ..... Plt./309

[56] References Cited

U.S. PATENT DOCUMENTS

P.P. 10,153 12/1997 van Andel ..... Plt./309
P.P. 10,836 3/1999 van Andel ..... Plt./309

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 87F652-1 as seed parent and 85T305-1 as pollen parent. The varietal denomination of the new variety is 'Stalsimo'.

The first act of asexual reproduction of 'Stalsimo' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Stalsimo' are firmly fixed and retained through successive generations.

SUMMARY OF THE INVENTION

The new variety of Alstroemeria, 'Stalsimo', produces large flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Stalsimo' has not been observed under all possible environmental conditions. Phenotypic expression may vary with variations in environment such as temperature, light intensity, day length and growing and cultural conditions.

Botanical classification:
- *Family.*—Amaryllidaceae.
- *Genus.*—Alstroemeria sp.

Plant:
- *Form.*—Bush.
- *Shape.*—Upright.
- *Height.*—About 150 to 180 cm.
- *Growth rate.*—Medium.

- *Main stem length.*—About 170 cm.
- *Internode length.*—About 1 to 8 cm.
- *Growth.*—Vigorous.
- *Strength.*—Strong.
- *Blooming habit.*—Continuous; blooms profusely throughout the year.
- *Rhizomes.*—Plant about 1 to 2 years old. Color: Near 155D. Size: About 10 to 30 cm.

Foliage:
- *Number of leaves.*—About 20 to 30 per stem.
- *Size of leaf.*—Length: About 15 to 20 cm. Width: About 3 to 5 cm.
- *Shape of leaf.*—Elliptic.
- *Margin.*—Straight.
- *Texture.*—Glossy.
- *Color.*—Upper side: Near 137A. Underside: Near 137C.

Flower:
- *Size (when first anthers release pollen).*—Diameter: About 7 cm. Depth: About 5 cm.
- *Borne.*—About 3 to 6 blooms per umbel.
- *Shape or form.*—When bloom first opens: Cup. When bloom matures: Cup.
- *Fragrance.*—None.
- *Lasting quality.*—On plant: About 4 weeks. As cut flower: About 16–18 days.
- *Tepalage.*—Number of tepals: About 6. Arrangement: 2 concentric circles of 3 tepals. Shape: Inner tepals, long obovate; outer tepals, obovate. Margin: Minutely crimped. Apex: Pointed. Lastingness on plant: Stay on stem about 4 weeks. Texture: Soft. Appearance: Velvety.
- *Color.*—Outer tepals — body near 53C, base near 54C, about 0–5 spots, near 185A, underside near 53C. Inner median tepal — near 53C, base near 54C, about 20–30 spots, near 185A, underside near 53C. Inner lateral tepals — body near 53A with area of about 6A as illustrated, base near 54C, about 20–50 spots, near 185A, underside near 53C with area of 6A similar to tepal upper surface.

Flower stem:
- *Peduncle length.*—About 10 to 15 cm. Color: Near 137B. Strength: Strong, erect. Upright: Yes. Discoloration: No discoloration after full bloom, not hairy.
- *Persistence.*—Flower does not hang on and dry.
- *Disease resistance.*—Unknown.

Bud:

*Size.*—Diameter: About 1 to 2 cm. Depth or length: About 2 to 4 cm.

*Form.*—Pear-shaped.

*Rate of opening.*—Fast.

*Color of tepals when tepals first divide.*—Near 53C.

*Color of tepals when tepals begin to unfurl.*—Near 53C.

Reproductive organs:

*Stamen.*—Number: About 6. Arrangement: Side by side around the style.

*Anthers.*—Size: About 8 to 10 mm. Color: Near 53A.

*Filaments.*—Length: 5 cm. Color: Near 53C.

*Pollen.*—Color: Near 165B.

*Pistils.*—1. Styles: Length about 4 to 5 cm. Color: Near 53C.

*Stigmas.*—Color: Near 53C.

Fruit: Fertile.

*Shape.*—Round.

*Color at maturity.*—Near 163A.

I claim:

1. A new and distinct Alstroemeria plant of the variety substantially as shown and described.

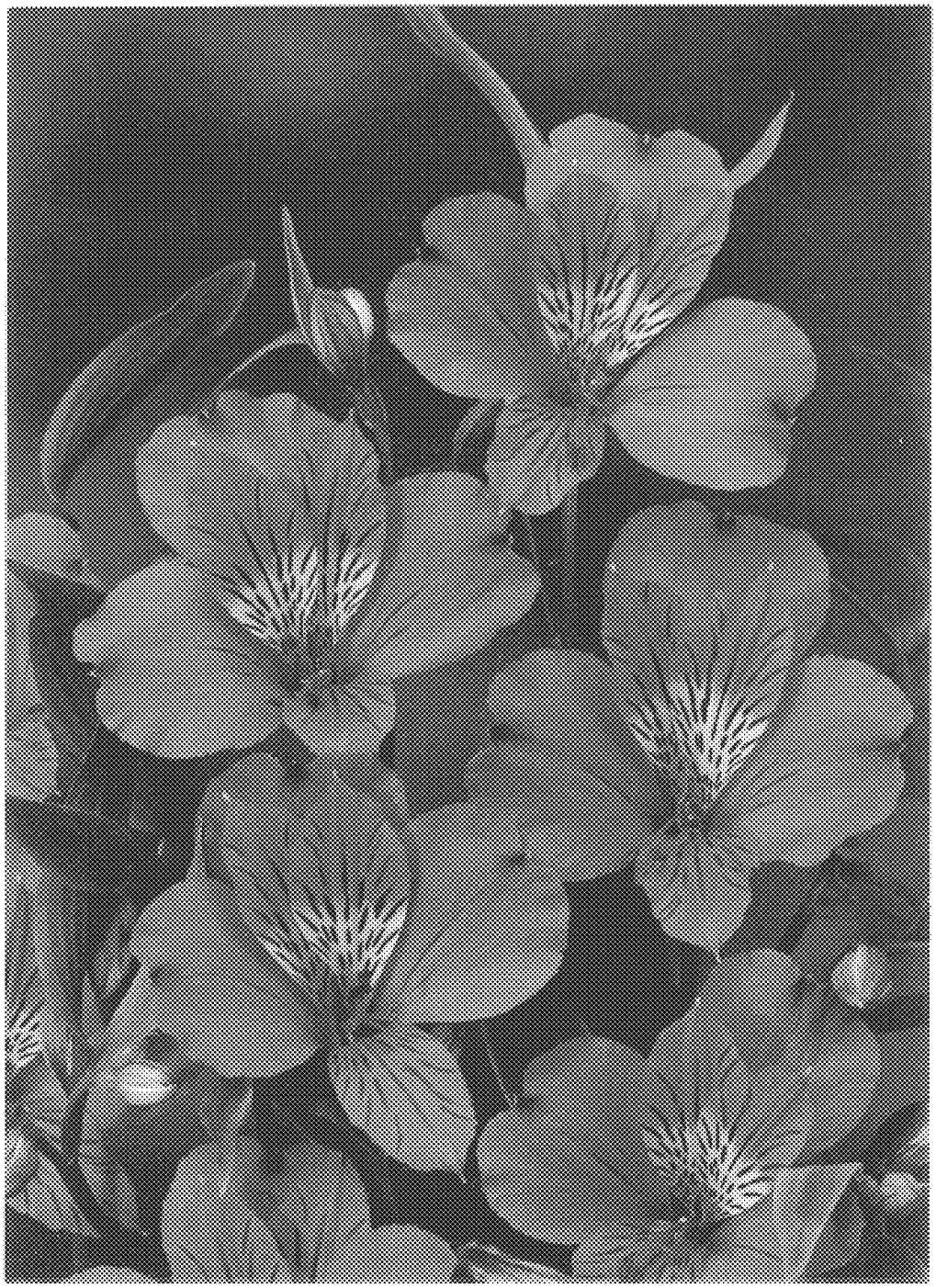

* * * * *